US012797149B2

(12) United States Patent
Hasegawa

(10) Patent No.: US 12,797,149 B2

(45) Date of Patent: Nov. 17, 2026

(54) MEDICAL MANIPULATOR SYSTEM AND ACCESS DEVICE

(71) Applicant: OLYMPUS CORPORATION, Tokyo (JP)

(72) Inventor: Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 969 days.

(21) Appl. No.: 18/158,865

(22) Filed: Jan. 24, 2023

(65) Prior Publication Data

US 2023/0157778 A1 May 25, 2023

Related U.S. Application Data

(63) Continuation of application No. PCT/JP2020/029654, filed on Aug. 3, 2020.

(51) Int. Cl.
*A61B 34/00* (2016.01)
*A61B 34/30* (2016.01)

(52) U.S. Cl.
CPC ........ *A61B 34/70* (2016.02); *A61B 2034/301* (2016.02)

(58) Field of Classification Search
CPC ............ A61B 17/3421; A61B 17/3439; A61B 17/3494; A61B 2017/3464; A61B 34/70; A61B 2034/301; A61M 25/0023; A61M 2025/0006; A61M 2025/0004
See application file for complete search history.

(56) References Cited

U.S. PATENT DOCUMENTS

| | | | | |
|---|---|---|---|---|
| 5,882,293 | A | 3/1999 | Ouchi | |
| 6,352,503 | B1 | 3/2002 | Matsul et al. | |
| 2005/0251111 | A1 | 11/2005 | Saito et al. | |
| 2008/0119872 | A1 * | 5/2008 | Brock .................... | A61B 34/30 606/130 |

(Continued)

FOREIGN PATENT DOCUMENTS

| | | | | |
|---|---|---|---|---|
| CN | 109331325 A | * | 2/2019 | ........ A61M 25/0023 |
| CN | 114903600 A | * | 8/2022 | ....... A61B 17/00234 |

(Continued)

OTHER PUBLICATIONS

"International Application Serial No. PCT/JP2020/029654, International Search Report dated Sep. 24, 2020", w/ English Translation, (Sep. 24, 2020), 5 pgs.

*Primary Examiner* — Ashley L Fishback
(74) *Attorney, Agent, or Firm* — Schwegman Lundberg & Woessner, P.A.

(57) ABSTRACT

The medical manipulator system includes: a treatment tool having a long flexible shaft and a rigid shaft; an access device having a long flexible tube, into which the flexible shaft is inserted, and a rigid sheath, into which the shafts are inserted; and a resistance generating part that is provided on at least one of the rigid shaft and the sheath and that generates resistance to advancing of the rigid shaft through the sheath. The resistance generated by the resistance generating part increases when a distal end of the advancing treatment tool passes through a distal end of the flexible tube or a vicinity thereof, and the resistance generated by the resistance generating part decreases after the distal end of the advancing treatment tool passes through the distal end of the flexible tube or the vicinity thereof.

8 Claims, 13 Drawing Sheets

(56) References Cited

U.S. PATENT DOCUMENTS

| | | | |
|---|---|---|---|
| 2015/0282835 | A1 | 10/2015 | Castro et al. |
| 2018/0021060 | A1 | 1/2018 | Castro et al. |

FOREIGN PATENT DOCUMENTS

| | | | |
|---|---|---|---|
| EP | 0834278 | A1 | 4/1998 |
| EP | 1588670 | A1 | 10/2005 |
| JP | 10234742 | | 9/1998 |
| JP | 10248800 | A | 9/1998 |
| JP | 2000033071 | A | 2/2000 |
| JP | 2001120558 | A | 5/2001 |
| JP | 3306330 | B2 | 7/2002 |
| JP | 2004154485 | A | 6/2004 |
| JP | 3806518 | B2 | 8/2006 |
| JP | 2012016530 | A | 1/2012 |
| JP | 2017169777 | A | 9/2017 |
| WO | WO-2017163876 | A1 | 9/2017 |

* cited by examiner

MEDICAL MANIPULATOR SYSTEM AND ACCESS DEVICE

This is a continuation of International Application PCT/JP2020/029654 which is hereby incorporated by reference herein in its entirety.

TECHNICAL FIELD

The present invention relates to a medical manipulator system and an access device.

BACKGROUND ART

A known access device in the related art is attached to the outside of an endoscope and guides a treatment tool (for example, see PTLs 1 and 2).

In the case of a treatment tool having a flexible shaft with high flexibility, a doctor needs to hold an operation part of the treatment tool with one hand and support the flexible shaft with the other hand in order to prevent the flexible shaft from bending. Hence, it is difficult for one doctor to operate two flexible treatment tools simultaneously.

PTL 2 discloses a rigid shaft provided at the proximal end of a treatment tool and a rigid sheath provided at the proximal end of an access device and supporting the rigid shaft. Because the combination of the rigid shaft and the rigid sheath eliminates the need for a doctor to support the flexible shaft with the other hand, the aforementioned disadvantage is eliminated.

CITATION LIST

Patent Literature

{PTL 1} Publication of Japanese Patent No. 3806518

{PTL 2} U.S. Patent Application Publication No. 2018/0021060

SUMMARY OF INVENTION

According to an aspect of the present invention, there is provided a medical manipulator system including: a treatment tool having a long flexible shaft and a rigid shaft connected to a proximal end of the flexible shaft; an access device that guides the treatment tool and that has a long flexible tube, into which the flexible shaft is inserted, and a rigid sheath, which is connected to a proximal end of the flexible tube and into which the flexible shaft and the rigid shaft are inserted; and a resistance generating part that is provided on at least one of the rigid shaft and the sheath and that generates resistance to advancing of the rigid shaft through the sheath. The resistance generated by the resistance generating part increases when a distal end of the advancing treatment tool passes through a distal end of the flexible tube or a vicinity of the distal end of the flexible tube inside the flexible tube, and the resistance generated by the resistance generating part decreases after the distal end of the advancing treatment tool passes through the distal end of the flexible tube or the vicinity.

According to another aspect of the present invention, there is provided an access device that guides a treatment tool, the access device including: a long flexible tube; a sheath that is connected to a proximal end of the flexible tube; and a resistance generating part that generates resistance when the treatment tool is inserted. The resistance generated by the resistance generating part increases when a distal end of the advancing treatment tool passes through a distal end of the flexible tube or a vicinity of the distal end of the flexible tube inside the flexible tube, and the resistance generated by the resistance generating part decreases after the distal end of the advancing treatment tool passes through the distal end of the flexible tube or the vicinity.

DESCRIPTION OF EMBODIMENTS

A medical manipulator system 100 according to an embodiment of the present invention will be described below with reference to the drawings.

Figure 1:
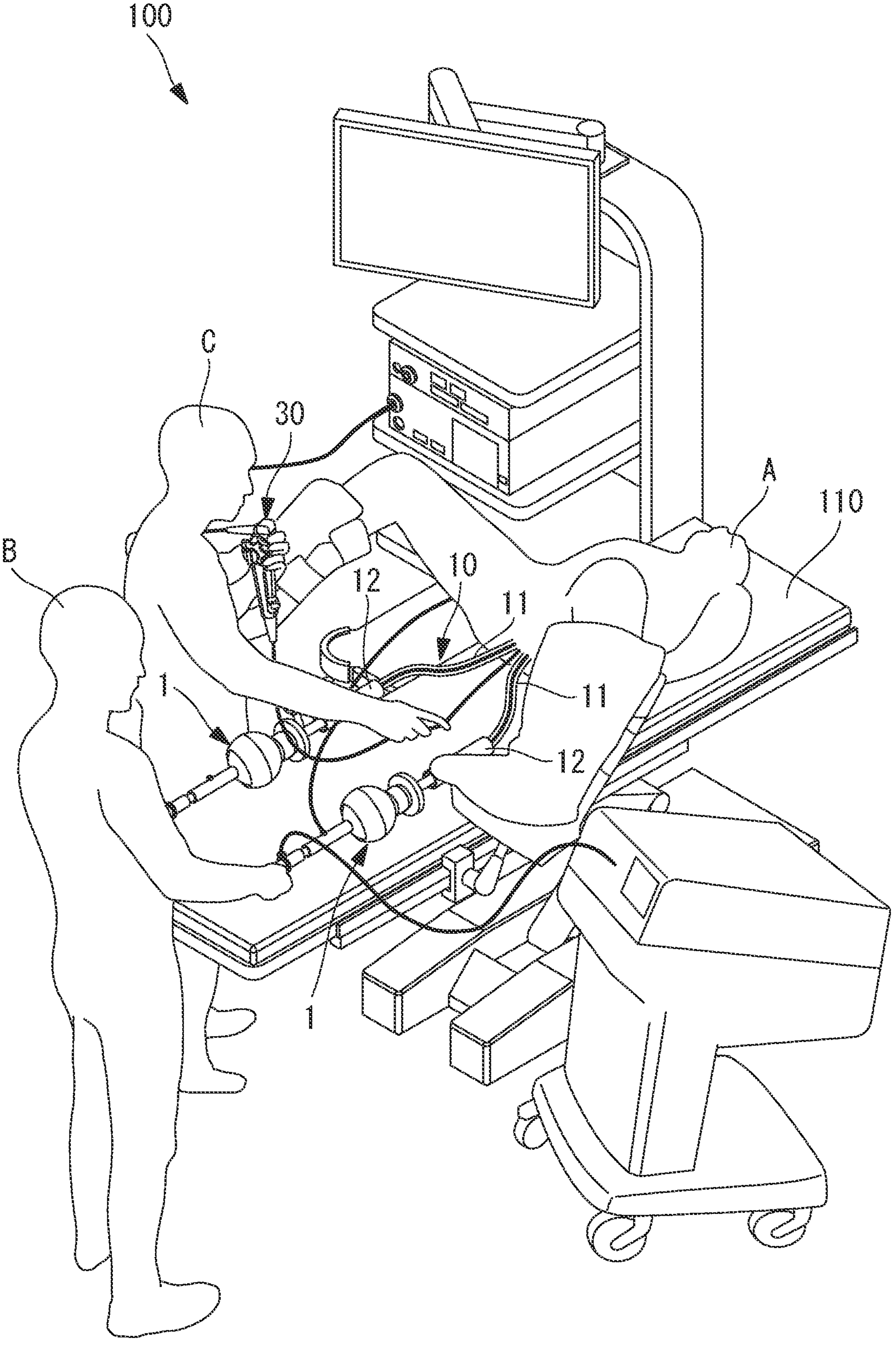
FIG. 1 is a diagram showing an example of surgery using a medical manipulator system according to an embodiment of the present invention.
Figure 2:
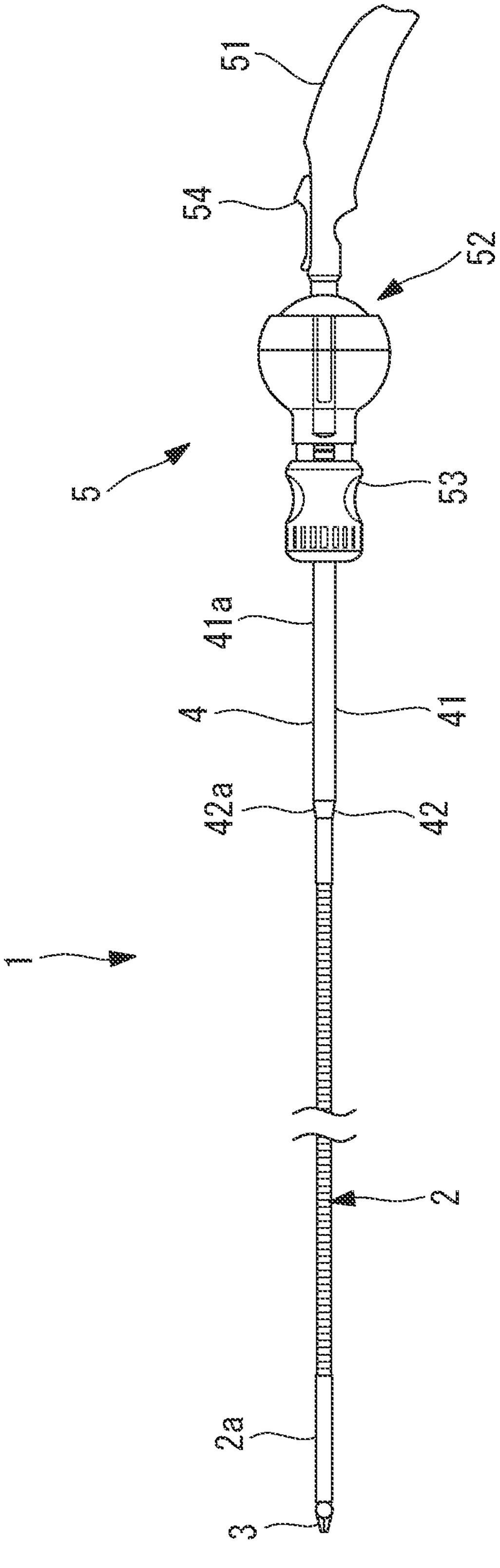
FIG. 2 shows the overall configuration of a treatment tool according to the embodiment of the present invention.
Figure 3:
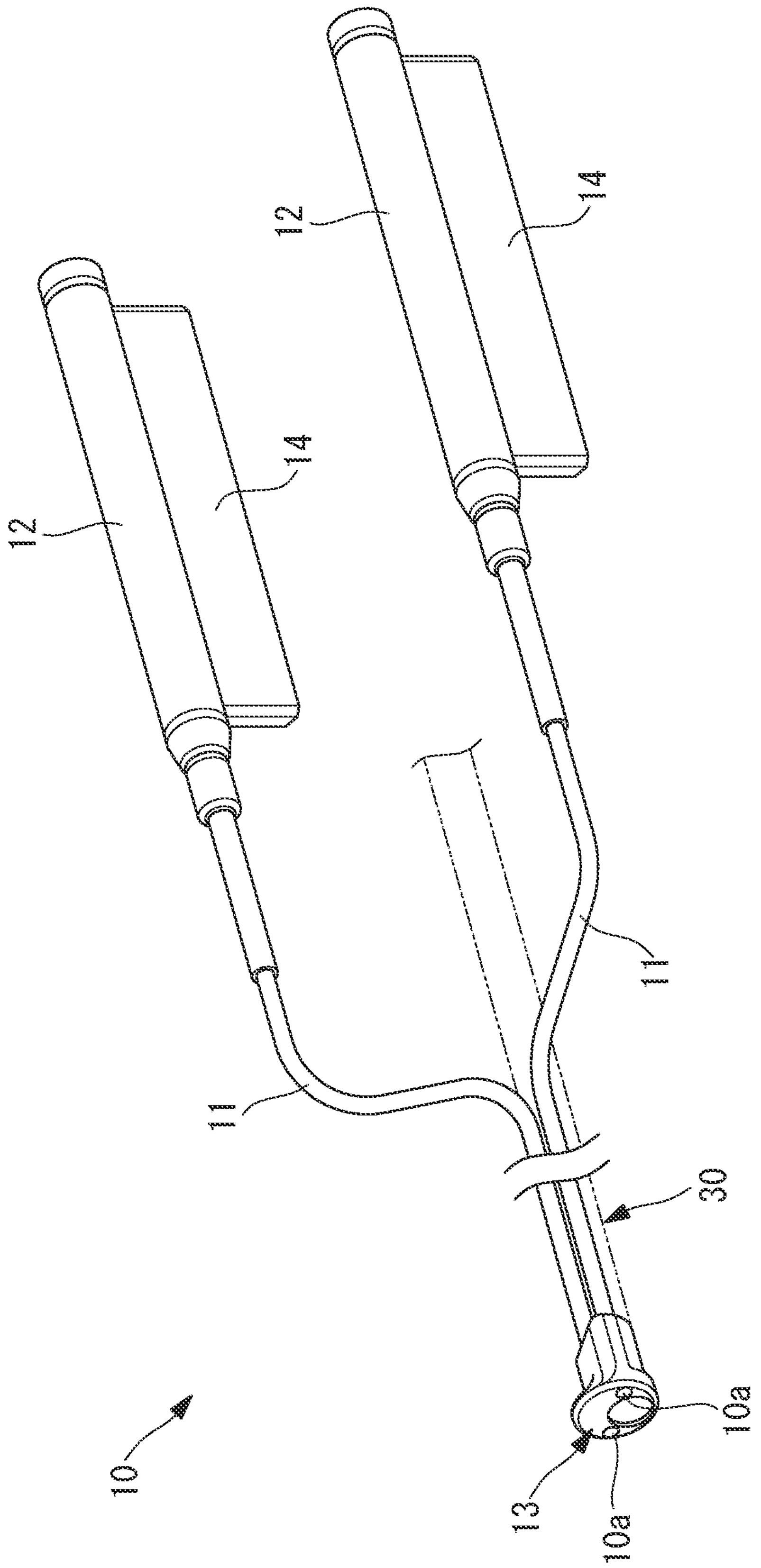
FIG. 3 shows the overall configuration of an access device according to the embodiment of the present invention.

FIG. 1 shows an example of use of the medical manipulator system 100 according to this embodiment. The medical manipulator system 100 is used in combination with an endoscope 30 and, as shown in FIGS. 1 to 3, includes a treatment tool 1 and an access device 10 that is externally attached to the endoscope 30 and guides the treatment tool 1. The treatment tool 1 and the access device 10 are inserted together with the endoscope 30 into the anus of a patient A lying on an operating table 110. The treatment tool 1 is operated by a doctor B, and the endoscope 30 is operated by a scopist C.

As shown in FIG. 2, the treatment tool 1 includes a long flexible shaft 2 having flexibility, an end effector 3 connected to the distal end of the flexible shaft 2, a rigid shaft 4 connected to the proximal end of the flexible shaft 2, and an operation unit 5 connected to the proximal end of the rigid shaft 4.

The end effector 3 is a portion that acts on a biological tissue and is, for example, a high-frequency knife or grasping forceps.

The flexible shaft 2 is a portion to be inserted into the body, and a bending portion 2*a* is provided at the distal end of the flexible shaft 2. The rigid shaft 4 extends coaxially with the flexible shaft 2, and the rigid shaft 4 and the operation unit 5 are disposed outside the body of the patient A.

The rigid shaft 4 includes a cylindrical shaft body 41 and a tapered portion 42 connected to the distal end of the shaft body 41. The rigid shaft 4 is formed of a hard material, such as a hard resin or a metal.

The outer diameter of the shaft body 41 is uniform and is larger than the outer diameter of the flexible shaft 2, and an outer circumferential surface (parallel surface) 41*a* of the shaft body 41 is parallel to the longitudinal axis of the shaft body 41.

The tapered portion 42 has a truncated cone shape whose diameter gradually decreases toward the side of the distal end, and an outer circumferential surface (inclined surface) 42*a* of the tapered portion 42 is inclined so as to be gradually displaced radially outward from the side of the distal end toward the side of the proximal end with respect to the longitudinal axis of the rigid shaft 4. The outer diameter of the proximal end of the outer circumferential surface 42*a* is equal to the outer diameter of the outer circumferential surface 41*a*, and the outer circumferential surface 41*a* extends from the proximal end of the outer circumferential surface 42*a* toward the side of the proximal end of the rigid shaft 4. The tapered portion 42 may have a shape other than a truncated cone and may have, for example, a hemispherical shape or a stepped shape.

The operation unit 5 includes an operation handle 51 to be held by a hand of the doctor B. The doctor B can advance the entire treatment tool 1 by pushing the operation handle 51 toward the side of the distal end and can retract the entire treatment tool 1 by pulling the operation handle 51 toward the side of the proximal end.

The operation handle 51 is supported by a ball joint structure 52 between the rigid shaft 4 and the operation handle 51 so as to be tiltable in any direction with respect to the longitudinal axis of the rigid shaft 4. The operation handle 51 is connected to the bending portion 2*a* by a wire passing through the inside of the shafts 2 and 4, and the bending portion 2*a* is configured to bend in accordance with the tilting direction and tilting angle of the operation handle 51.

The operation unit 5 may be further provided with a rotation operation part 53 for integrally rotating the end effector 3, the flexible shaft 2, and the rigid shaft 4 about the longitudinal axes of the shafts 2 and 4.

The operation unit 5 may be further provided with a structure correspond in to the type of the end effector 3. For example, when the end effector 3 is grasping forceps, a slider 54 for opening and closing the grasping forceps may be provided.

As shown in FIG. 3, the access device 10 includes a long tubular flexible tube 11 having flexibility and a rigid tubular holder (sheath) 12 connected to the proximal end of the flexible tube 11.

The distal end of the flexible tube 11 is fixed to an attachment part 13 attached to the distal end of the endoscope 30. The attachment part 13 is, for example, an annular or cylindrical cap fitted to the outside of the distal end of the endoscope 30. By attaching the attachment part 13 to the distal end of the endoscope 30, the access device 10 is attached to the endoscope 30 such that the flexible tube 11 is parallel to the endoscope 30. As in the example in FIG. 1, when two treatment tools 1 are to be inserted into the body together with one endoscope 30, the access device 10 may have two flexible tubes 11 connected to one attachment part 13.

The holder 12 extends coaxially with the flexible tube 11, and the inner hole of the flexible tube 11 and the inner hole of the holder 12 form a treatment tool channel 10*a* (see FIG. 5), which extends from the proximal end face of the holder 12 to the distal end face of the flexible tube 11 and into which the treatment tool 1 is inserted. The inner diameter of the flexible tube 11 is larger than the outer diameter of the flexible shaft 2, so that the flexible shaft 2 can be inserted through the flexible tube 11. The inner diameter of the holder 12 is larger than the outer diameter of the rigid shaft 4, so that the flexible shaft 2 and the shaft 4 can be inserted through the holder 12.

A fixing portion 14 for fixing the holder 12 to the operating table 110 is fixed to the holder 12. By inserting the rigid shaft 4 into the holder 12 fixed to the operating table 110 at the fixing portion 14, the treatment tool 1 is supported by the holder 12, and the rigid shaft 4 is guided by the holder 12 in the longitudinal direction of the holder 12. Accordingly, it is possible for one doctor to easily operate two treatment tools 1.

Figure 4A:
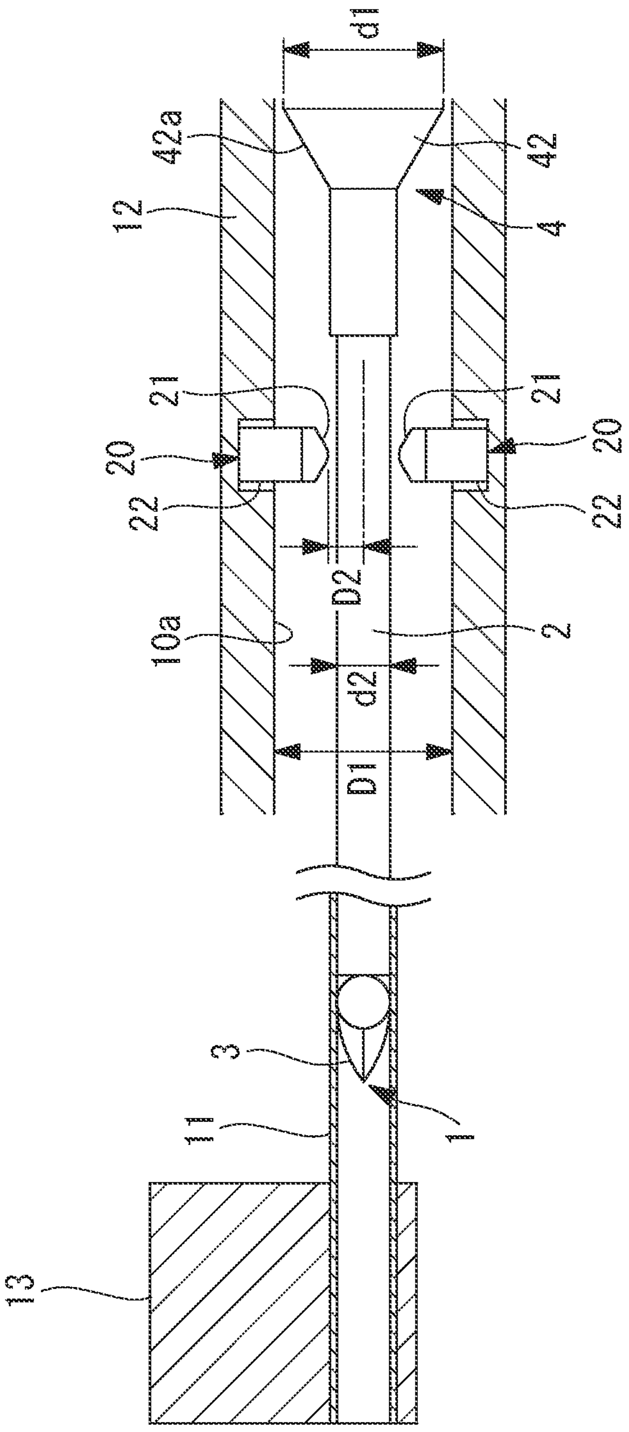
FIG. 4A is a diagram for explaining the operation of the medical manipulator system.
Figure 4B:
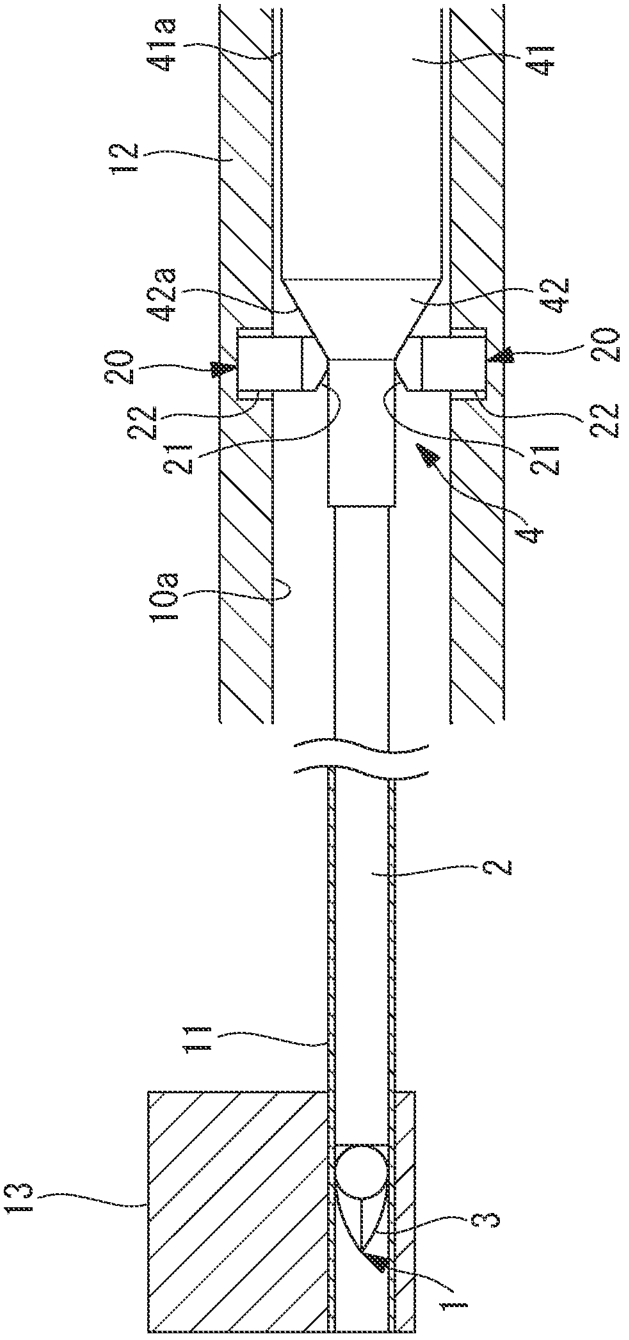
FIG. 4B is a diagram for explaining the operation of the medical manipulator system.
Figure 4C:
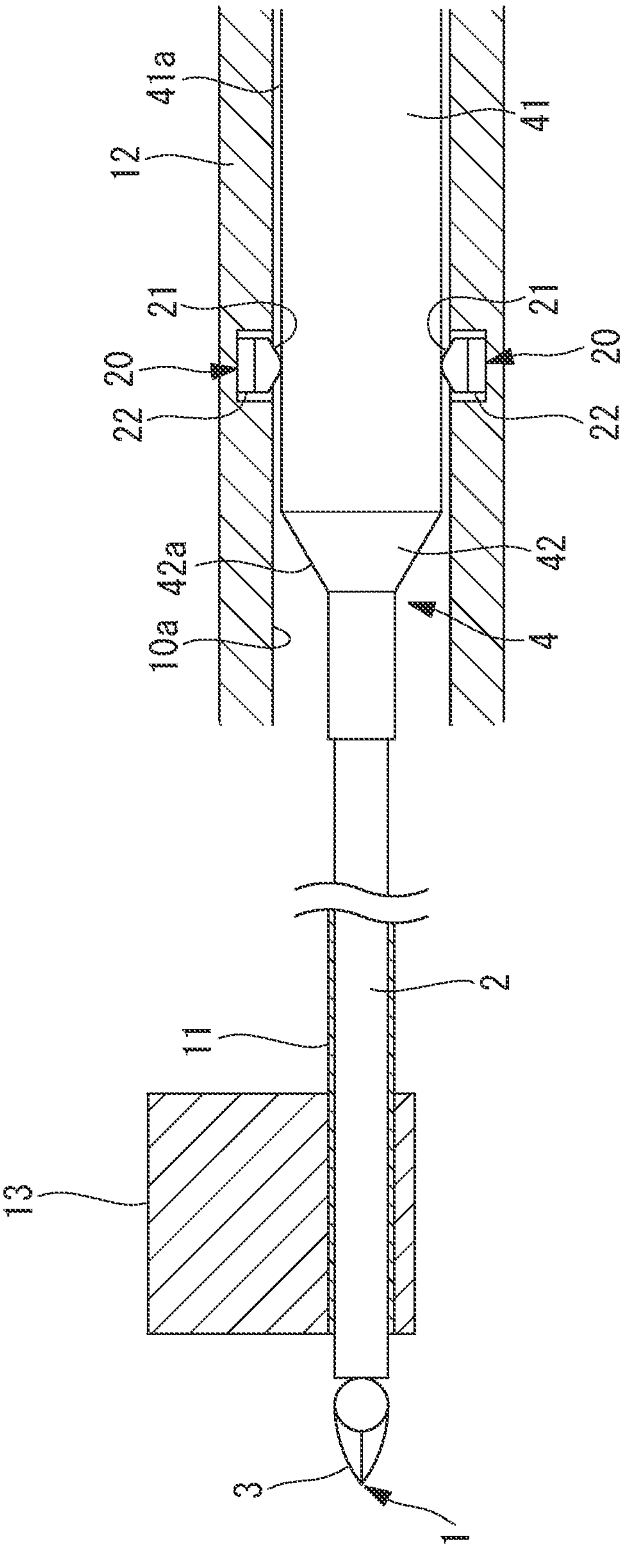
FIG. 4C is a diagram for explaining the operation of the medical manipulator system.

As shown in FIGS. 4A to 4C, the medical manipulator system 100 further includes resistance generating parts 20 that are, provided on the holder 12 of the access device 10 and that generate resistance to the advancing of the rigid shaft 4 through the holder 12.

The resistance generating parts 20 are spring plungers protruding radially inward from the inner circumferential surface of the holder 12. The resistance generating parts 20 include movable bodies 21, such as balls or pins, and elastic members 22, such as springs, that urge the movable bodies 21 inward in the radial direction of the holder 12. The elastic members 22 are accommodated in recesses formed in the inner circumferential surface of the holder 12. The ends of the movable bodies 21 are spherical.

As shown in FIG. 4A, while the elastic members 22 are in a natural state, the distance from the longitudinal axis of the holder 12 (or the longitudinal axis of the treatment tool channel 10*a*) to the end of a resistance generating part 20 is larger than the radii of the end effector 3 and the flexible shaft 2 and is smaller than the radius of the shaft body 41. Accordingly, the resistance generating parts 20 do not come into contact with the outer circumferential surfaces of the end effector 3 and the flexible shaft 2 but come into contact with the outer circumferential surfaces 41*a* and 42*a* of the rigid shaft 4.

Specifically, the positions of the resistance generating parts 20 satisfy the following relationship:

$$D1>d1>D2\times 2>d2,$$

where D1 is the inner diameter of the holder 12, D2 is the distance from the longitudinal axis of the holder 12 to a resistance generating part 20 in the radial direction when the elastic member 22 is in a natural state, d1 the outer diameter of the shaft body 41 of the rigid shaft 4, and d2 is the outer diameter of the flexible shaft 2.

The resistance generating parts 20 generate resistance to the advancing of the rigid shaft 4 through the holder 12 by making contact with the outer circumferential surface 42*a* of the tapered portion 42. Specifically, the movable bodies 21 are pressed outward in the radial direction of the holder 12 by the outer circumferential surface 42*a*, and the elastic members 22, which elastically contract in the radial direction of the holder 12, generate an elastic restoring force. Because the outer circumferential surface 42*a* is inclined with respect to the longitudinal axis of the rigid shaft 4, a component force of the elastic restoring force is generated in the longitudinal direction of the rigid shaft 4, and this component force serves as resistance. Furthermore, the friction between the movable bodies 21 and the outer circumferential surface 42*a* also serves as resistance.

A doctor operating the treatment tool 1 feels the force generated in the resistance generating parts 20 through the rigid shaft 4 and the operation unit 5, which are made of a rigid material. Hence, the resistance generated in the resistance generating parts 20 is efficiently transmitted to the hand of the doctor holding the operation handle 51, and the doctor can clearly feel resistance.

The resistance generating parts 20 may also be configured to come into light contact with the outer circumferential surfaces of the end effector 3 and the flexible shaft 2.

As shown in FIG. 4B, in the longitudinal direction of the holder 12, the resistance generating parts 20 are provided at such positions that the tapered portion 42 of the rigid shaft 4 passes through the resistance generating parts 20 when the distal end of the treatment tool 1 advancing through the treatment tool channel 10*a* passes through the distal end of the flexible tube 11 or the vicinity of the distal end of the flexible tube 11 inside the flexible tube 11.

Specifically, the resistance generating parts 20 generate large resistance based on the elastic restoring force and the friction when the distal end of the treatment tool 1 advancing through the treatment tool channel 10*a* passes through the distal end or the vicinity of the distal end of the flexible tube 11. Meanwhile, the resistance generating parts 20 do not generate resistance until the distal end of the treatment tool 1 advancing through the treatment tool channel 10*a* reaches the distal end or the vicinity of the distal end of the flexible tube 11. Hence, the doctor can recognize that the distal end of the treatment tool 1 has reached the distal end of the flexible tube 11 or the vicinity thereof on the basis of an increase in the resistance felt by the hand gripping the operation handle 51.

Figure 5:
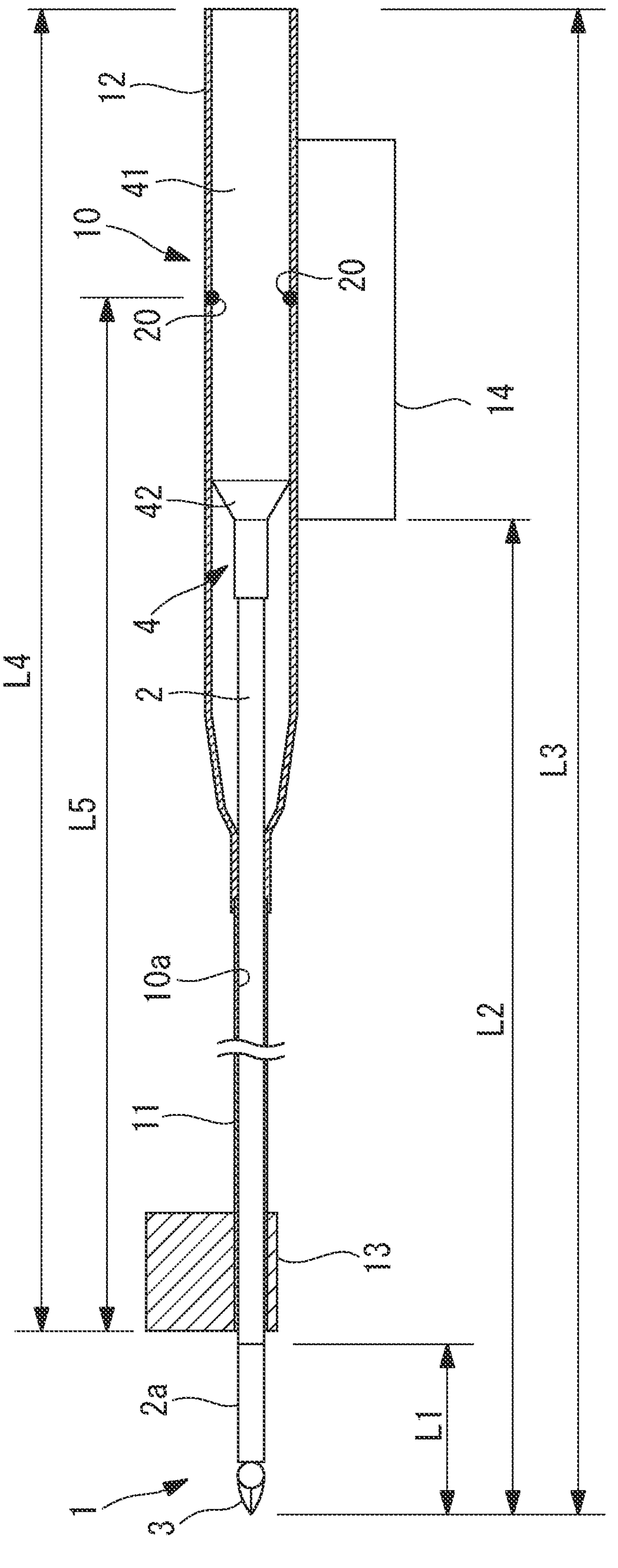
FIG. 5 is a diagram for explaining design values of the treatment tool and the access device.

As shown in FIG. 5, the dimensions of the treatment tool 1 and the access device 10 in the longitudinal direction have the following relationship:

$$(L3-L1)\geq L4>L5\geq L2,$$

where L1 is the distance from the distal end of the treatment tool 1 to the proximal end of the bending portion 2*a*, L2 is the distance from the distal end of the treatment tool 1 to the proximal end of the tapered portion 42 (the distal end of the shaft body 41), L3 is the distance from the distal end of the treatment tool 1 to the proximal end of the rigid shaft 4, L4 is the distance from the distal end of the flexible tube 11 to the proximal end of the holder 12, and L5 is the distance from the distal end of the flexible tube 11 to the resistance generating parts 20.

Because L5 is larger than or equal to L2, the resistance generating parts 20 come into contact with the outer circumferential surface 42*a* of the tapered portion 42 inside the holder 12 to generate resistance before the distal end of the treatment tool 1 advancing through the flexible tube 11 protrudes from the distal end of the flexible tube 11.

Because L4 is larger than L5, the resistance generating parts 20 come into contact with the outer circumferential surface 42*a* of the tapered portion 42 after the rigid shaft 4 is inserted into the holder 12 in the process of inserting the treatment tool 1 into the access device 10. As a result, the rigid shaft 4 is supported by the holder 12, stabilizing the position of the treatment tool 1, and thus, the operability of advancing/retracting operations of the treatment tool 1 is improved.

Because L3−L1 is larger than or equal to L4, the end effector 3 and the bending portion 2*a* completely protrude from the distal end of the flexible tube 11 in a state in which the entire rigid shaft 4 is inserted through the holder 12. Hence, the end effector 3 can be moved without being restricted by the access device 10, and the treatment performance is stabilized.

Next, the operation of the medical manipulator system 100 will be described.

In order to treat the affected area in the body of the patient A using the medical manipulator system 100 according to this embodiment, a doctor attaches the attachment part 13 of the access device 10 to the distal end of the endoscope 30, inserts the treatment tool 1 into the treatment tool channel 10*a* from the opening at the proximal end of the holder 12, and advances the treatment tool 1 through the treatment tool channel 10*a* from the proximal end of the holder 12 toward the distal end of the flexible tube 11 by operating the operation handle 51 held in his/her hand.

As shown in FIG. 4A, the end effector 3 and the flexible shaft 2 pass through the holder 12 without touching the resistance generating parts 20. Hence, until the tapered portion 42 of the rigid shaft 4 reaches the resistance generating parts 20, the resistance to the advancing of the treatment tool 1 inside the treatment tool channel 10*a* is only the relatively small friction between the inner circumferential surface of the flexible tube 11 and the outer circumferential surface of the flexible shaft 2. The doctor B can smoothly advance the treatment tool 1 through the treatment tool channel 10*a*.

Then, as shown in FIG. 4B, when the distal end of the treatment tool 1 approaches the distal end of the flexible shaft 2, the outer circumferential surface 42*a* of the tapered portion 42 comes into contact with the resistance generating parts 20, and the resistance generating parts 20 generate resistance to the advancing of the rigid shaft 4. The doctor B feels an increase in the resistance to the advancing of the treatment tool 1 in his/her hand. While the resistance generating parts 20 are in contact with the outer circumferential surface 42*a*, the amount of compression and the elastic restoring force of the elastic members 22 gradually increase as the treatment tool 1 is advanced, and thus, the resistance further gradually increases. From an increase in the resistance, the doctor B can intuitively recognize the approach of the distal end of the treatment tool 1 to the vicinity of the distal end of the flexible tube 11.

As shown in FIG. 4C, the tapered portion 42 passes through the resistance generating parts 20 at the same or substantially the same time at which the distal end of the treatment tool 1 protrudes from the distal end of the flexible tube 11. Subsequently, the outer circumferential surface 41*a* of the shaft body 41 comes into contact with the resistance generating parts 20, and the treatment tool 1 advances while maintaining contact between the outer circumferential surface 41*a* and the resistance generating parts 20.

Also in a state in which the resistance generating parts 20 are in contact with the outer circumferential surface 41*a*, the elastic members 22 in the contracted state continue to generate the elastic restoring force. Note that, because the outer circumferential surface 41*a* is parallel to the longitudinal axis of the rigid shaft 4, a component force of the elastic restoring force is not generated in the longitudinal direction of the rigid shaft 4, and the resistance generated by the resistance generating parts 20 is only the friction between the movable bodies 21 and the outer circumferential surface 41*a*. Furthermore, because the amount of elastic compression of the elastic members 22 is constant, the magnitude of the friction is constant. Hence, after the distal end of the treatment tool 1 protrudes from the distal end of the flexible tube 11, the resistance generated by the resistance generating parts 20 decreases, and only small resistance having a certain magnitude is generated to the advancing of the treatment tool 1. The doctor can recognize that the end effector 3 at the distal end of the treatment tool 1 has protruded from the distal end of the flexible tube 11 from the decrease in the resistance felt by his/her hand.

As described above, in a state in which the end effector 3 is disposed outside the distal end of the flexible tube 11, the resistance generated by the resistance generating parts 20 is small. Hence, the doctor B can advance or retract the end effector 3 almost without feeling resistance, by advancing or retracting the treatment tool 1.

As described above, according to this embodiment, in the process of inserting the treatment tool 1 into the access device 10, the magnitude of the resistance generated by the resistance generating parts 20 changes with time in accordance with the position of the distal end of the treatment tool 1 with respect to the distal end or the flexible tube 11. Specifically, when the distal end of the treatment tool 1 is away from the distal end of the flexible tube 11, the resistance is zero, and when the distal end of the treatment tool 1 is near the distal end of the flexible tube 11, the resistance gradually increases, and the resistance becomes maximum when or immediately before the distal end of the treatment tool 1 protrudes from the distal end of the flexible tube 11. The resistance generated by the resistance generating parts 20 is efficiently transmitted by the rigid shaft 4 and the operation unit 5 to the hand of the doctor gripping the operation handle 51 near the resistance generating parts 20. Hence, the doctor who is operating the treatment tool 1 can reliably recognize the timing at which the distal end of the treatment tool 1 protrudes from the distal end of the flexible tube 11.

Furthermore, after the distal end of the treatment tool 1 has protruded from the distal end of the flexible tube 11, the resistance decreases to a certain magnitude. Hence, the end effector 3 disposed outside the flexible tube 11 can be moved smoothly.

Furthermore, the resistance generated by the resistance generating parts 20 to the retraction of the rigid shaft 4 inside the holder 12 is only the friction between the resistance generating parts 20 and the outer circumferential surfaces 41*a* and 42*a*, which is sufficiently small. Hence, when the treatment tool 1 is removed from the body through the treatment tool channel 10*a*, the doctor B can retract the treatment tool 1 almost without feeling resistance.

In this embodiment, the resistance generating parts 20 may have such shapes that they make point contact with the outer circumferential surface 41*a* and surface contact or line contact with the outer circumferential surface 42*a*. This can further increase the resistance when the resistance generating parts 20 are in contact with the outer circumferential surface 42*a* and can further reduce the resistance when the resistance generating parts 20 are in contact with the outer circumferential surface 41*a*.

For example, the movable bodies 21 may have a cone shape with a spherical end, and the side surfaces of the movable bodies 21 may be conical surfaces that make line contact with the outer circumferential surface 42*a* or may have concave surfaces that make surface contact with the outer circumferential surface 42*a*.

Although the resistance generating parts 20 are spring plungers having the elastic members 22 in this embodiment, instead, another form is also possible. For example, the entire resistance generating parts 20 may be elastic members that are made of an elastic material. The elastic material is, for example, a resin material having elasticity. The resin material may be rubber or a plastic having high lubricity, such as polyacetal or monomer-cast nylon.

Figure 6A:
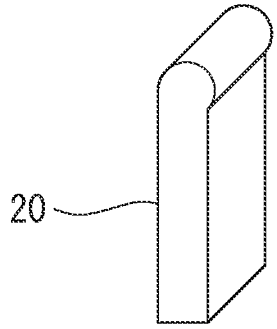
FIG. 6A is a diagram showing a modification of a resistance generating part.
Figure 6B:
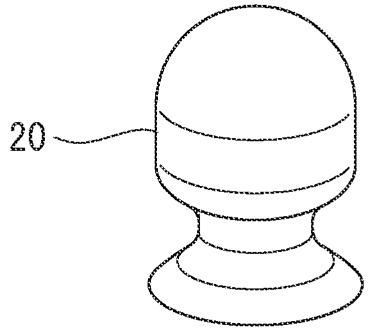
FIG. 6B is a diagram showing another modification of the resistance generating part.
Figure 6C:
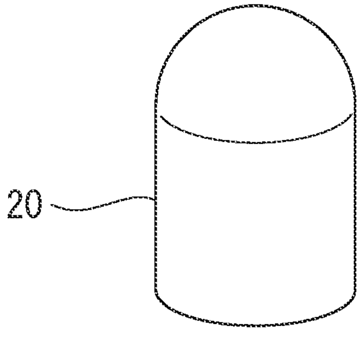
FIG. 6C is a diagram showing another modification of the resistance generating part.

FIGS. 6A to 6C show examples of the resistance generating part 20, the entirety of which is an elastic member. The resistance generating part 20 is elastically deformed in at least one of the longitudinal direction and the radial direction of the holder 12 by contact with the inclined surface 42*a*. The resistance generating parts 20 in FIGS. 6A and 6B are bent and laid down by contact with the outer circumferential surfaces 41*a* and 42*a*. The resistance generating part 20 in FIG. 6C is elastically compressed in the longitudinal direction of the resistance generating part 20, which corresponds to the radial direction of the holder 12, by contact with the outer circumferential surfaces 41*a* and 42*a*.

Although the rigid shaft 4 has the tapered portion 42 in this embodiment, the rigid shaft 4 may have no tapered portion 42. In that case, the resistance generating parts 20 may generate resistance by another means, instead of generating resistance by contact with the inclined surface 42*a*.

Figure 7:
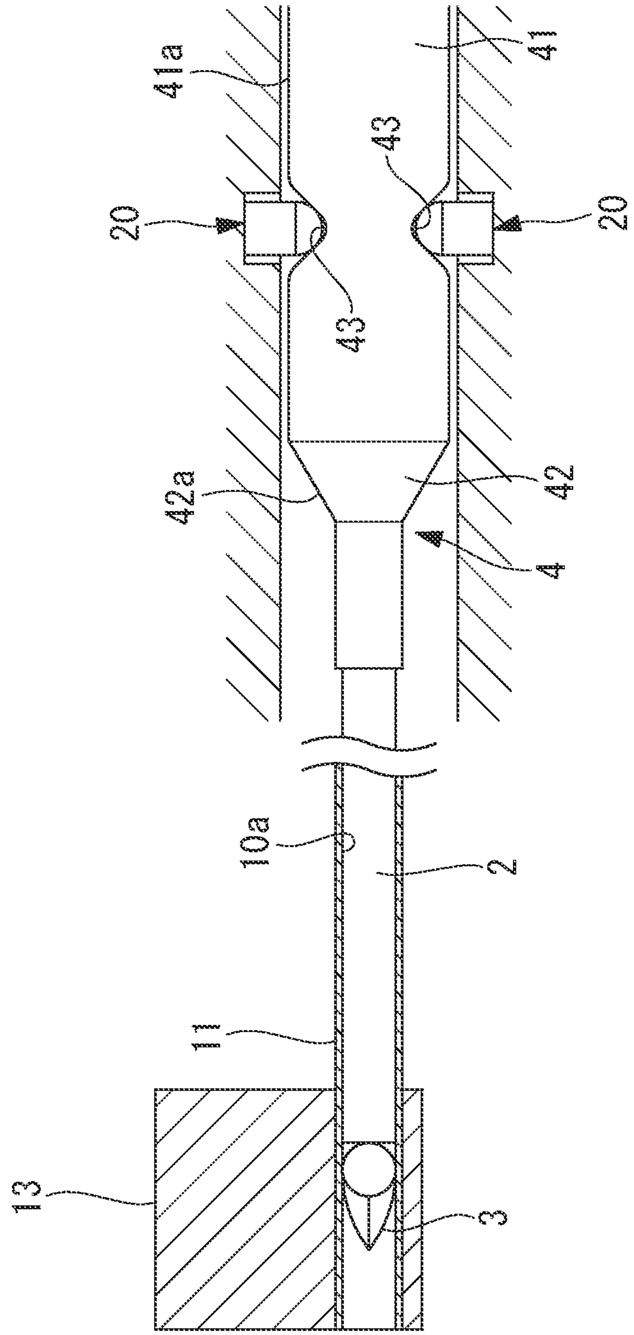
FIG. 7 is a partial side view of a modification of a rigid shaft of the treatment tool.

For example, as shown in FIG. 7, the resistance generating parts 20 may be configured to generate resistance by being fitted into a groove 43 in the outer circumferential surface 41*a*.

With this configuration, the resistance generating parts 20 generate a click feeling, serving as resistance, to both advancing and retraction of the rigid shaft 4 inside the holder 12. Hence, the doctor B can also recognize the timing at which the distal end of the treatment tool 1 retracted in the treatment tool channel 10*a* is retracted into the distal end of the flexible tube 11. Accordingly, in the process of removing the treatment tool 1, the doctor B can intuitively recognize that the end effector 3 has been completely stored in the flexible tube 11 from the click feeling.

Because the inner diameter D1 of the holder 12 is substantially equal to the outer diameter d1 of the rigid shaft 4, the clearance between the holder 12 and the flexible shaft 2 is large. Hence, in the process of inserting the treatment tool 1 into the access device 10, the flexible shaft 2 may meander in the holder 12. More specifically, due to the friction between the flexible shaft 2 and the flexible tube 11, the flexible shaft 2 is caught in the flexible tube 11, and a compressive force is applied to the flexible shaft 2 in the holder 12, making the flexible shaft 2 meander. However, because the doctor B cannot observe the flexible shaft 2 in the opaque holder 12, the doctor B may not notice the meandering of the flexible shaft 2. When the operation unit 5 is further pushed in with a strong force in a state in which the flexible shaft 2 meanders, buckling of the flexible shaft 2 occurs. Such meandering and buckling of the flexible shaft 2 are particularly likely to occur with the flexible shaft 2 having a small diameter and high flexibility. Meanwhile, in order to facilitate the ease of insertion of the flexible shaft 2 into a complexly curved body cavity, such as the large intestine, the flexible shaft 2 preferably has a small diameter and high flexibility.

Figure 8A:
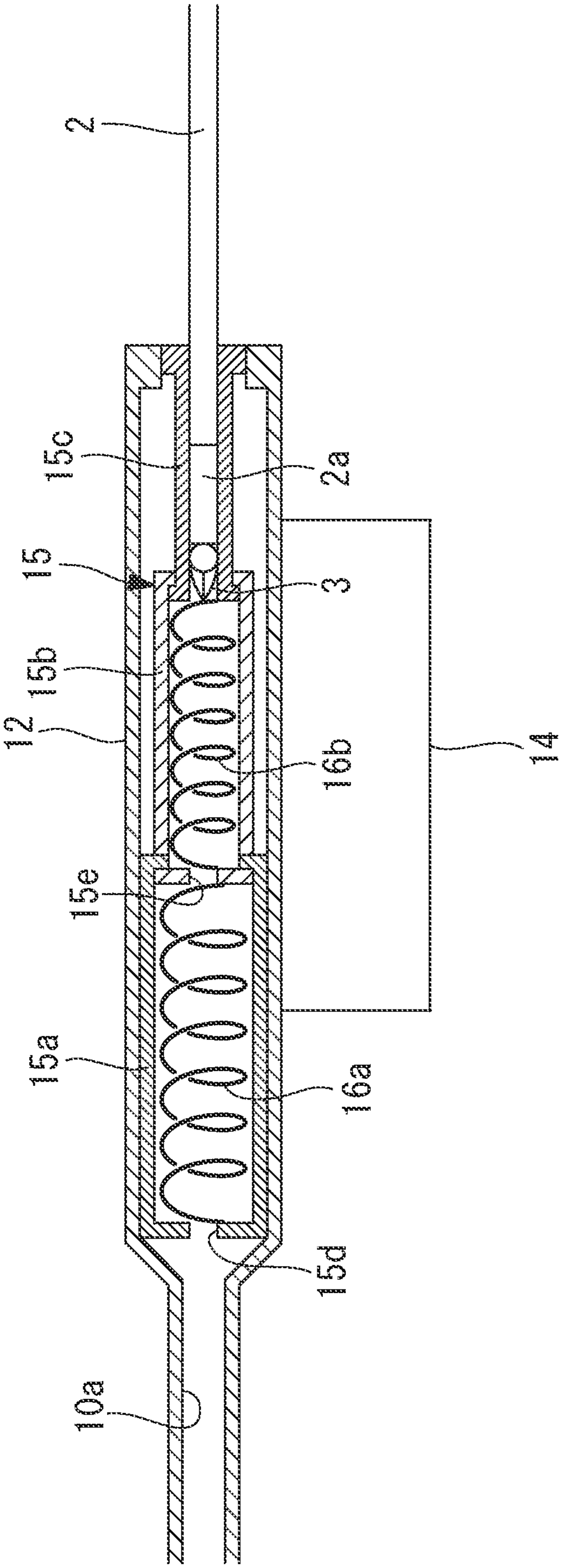
FIG. 8A is a partial longitudinal sectional view of a modification of the access device.
Figure 8B:
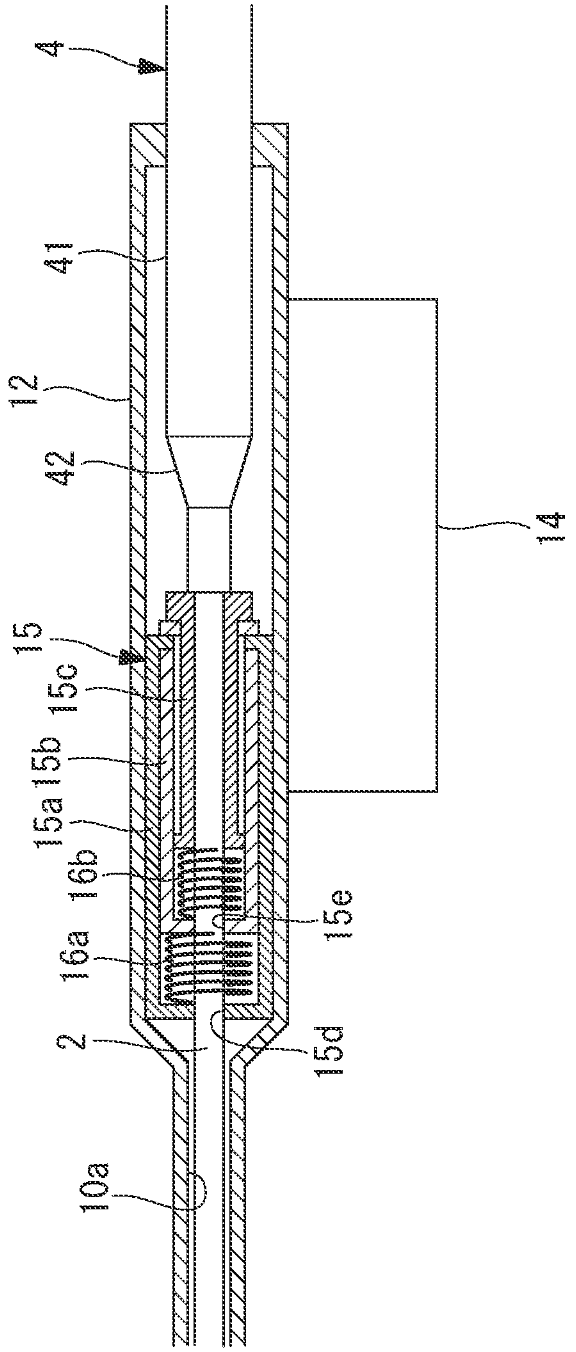
FIG. 8B is a partial longitudinal sectional view of the access device in FIG. 8A in a state in which a telescopic structure is contracted.

In this embodiment, in order to prevent buckling of the flexible shaft 2 in the holder 12, a telescopic structure 15 including two or more pipes may be provided in the holder 12, as shown in FIGS. 8A and 8B. The two or more pipes have different inner and outer diameters, are concentrically arranged, and are telescopically extendable in the longitudinal direction of the holder 12. FIGS. 8A and 8B show, as an example, the telescopic structure 15 including three pipes 15*a*, 15*b*, and 15*c*.

The outer pipe 15*a*, which has the largest outer diameter and is disposed on the outermost side, is disposed at the distal end of the holder 12 and is fixed to the holder 12. The other two pipes, 15*b* and 15*c*, are movable relative to the outer pipe 15*a* in the longitudinal direction of the holder 12. In a state in which the telescopic structure 15 is extended to the maximum, the proximal end of the inner pipe 15*c*, which has the smallest outer diameter and is arranged innermost, is disposed at or near the proximal end of the holder 12. The inner diameter of the inner pipe 15*c* is substantially equal to the outer diameter of the flexible shaft 2 and is smaller than the outer diameter of the rigid shaft 4.

A spring 16*a* for urging the intermediate pipe 15*b* toward the proximal end of the holder 12 is disposed between the pipes 15*a* and 15*b*, and a spring 16*b* for urging the inner pipe 15*c* toward the proximal end of the holder 12 is disposed between the pipes 15*b* and 15*c*. In a state in which no pressing force in the longitudinal direction is applied to the inner pipe 15*c*, the pipes 15*a*, 15*b*, and 15*c* are arranged in the fully extended state by the urging force of the springs 16*a* and 16*b*, as shown in FIG. 8A.

The flexible shaft 2 of the treatment tool 1 is inserted into the inner pipe 15*c* of the telescopic structure 15 in the fully extended state, and then, the rigid shaft 4 is inserted into the holder 12 while pressing the inner pipe 15*c* with the distal end of the rigid shaft 4 against the urging force of the springs 16*a* and 16*b*. When the telescopic structure 15 is in a fully contracted state, as shown in FIG. 8B, the end effector 3 and the bending portion 2*a* are disposed at positions outside the distal end of the flexible tube 11.

In this case, because the flexible shaft 2 is supported by the inner pipe 15*c* of the telescopic structure 15, meandering and buckling of the flexible shaft 2 in the holder 12 can be prevented. In particular, meandering and buckling are likely to occur at the proximal end portion of the flexible shaft 2, where the outer diameter sharply changes and the rigidity sharply changes. Hence, by supporting the proximal end portion of the flexible shaft 2 with the inner pipe 15*c*, meandering and buckling of the flexible shaft 2 can be effectively prevented.

In a state in which the rigid shaft 4 is inserted through the holder 12, the rigid shaft 4 is subjected to an urging force in a direction in which the rigid shaft 4 is retracted from the compressed springs 16*a* and 16*b*. The urging force of the springs 16*a* and 16*b* is preferably set to be smaller than the friction between the flexible shaft 2 and the flexible tube 11. By doing so, the rigid shaft 4 can be held at a fixed position against the urging force of the springs 16*a* and 16*b* when the doctor B releases his/her hand from the treatment tool 1 in a state in which the rigid shaft 4 is disposed in the holder 12.

In order that the flexible shaft 2 is supported not only by the inner pipe 15*c* but also by the intermediate pipe 15*b* and the outer pipe 15*a*, the diameters of through-holes 15*d* and 15*e* at the ends of the pipes 15*a* and 15*b*, respectively, are preferably substantially equal to the outer diameters of the flexible shaft 2. With this configuration, it is possible to control the shape of the flexible shaft 2 in the holder 12 to a linear shape with the through-holes 15*d* and 15*e* and to more reliably prevent meandering and buckling of the flexible shaft 2.

As the amount of insertion of the rigid shaft 4 into the holder 12 increases, the amount of contraction of the springs 16*a* and 16*b* increases. When the elastic restoring force of the springs 16*a* and 16*b* increases in accordance with the amount of contraction, the rigid shaft 4 needs to be inserted with a greater amount of operation force as the rigid shaft 4 is advanced through the holder 12.

In order to prevent the change in the amount of operation force like this, the springs 16*a* and 16*b* are preferably constant-load springs, which generate a constant elastic restoring force regardless of the amount of contraction. By using the constant-load spring, the rigid shaft 4 can be inserted into the holder 12 with a constant amount of operation force, regardless of the amount of insertion of the rigid shaft 4.

Figure 9:
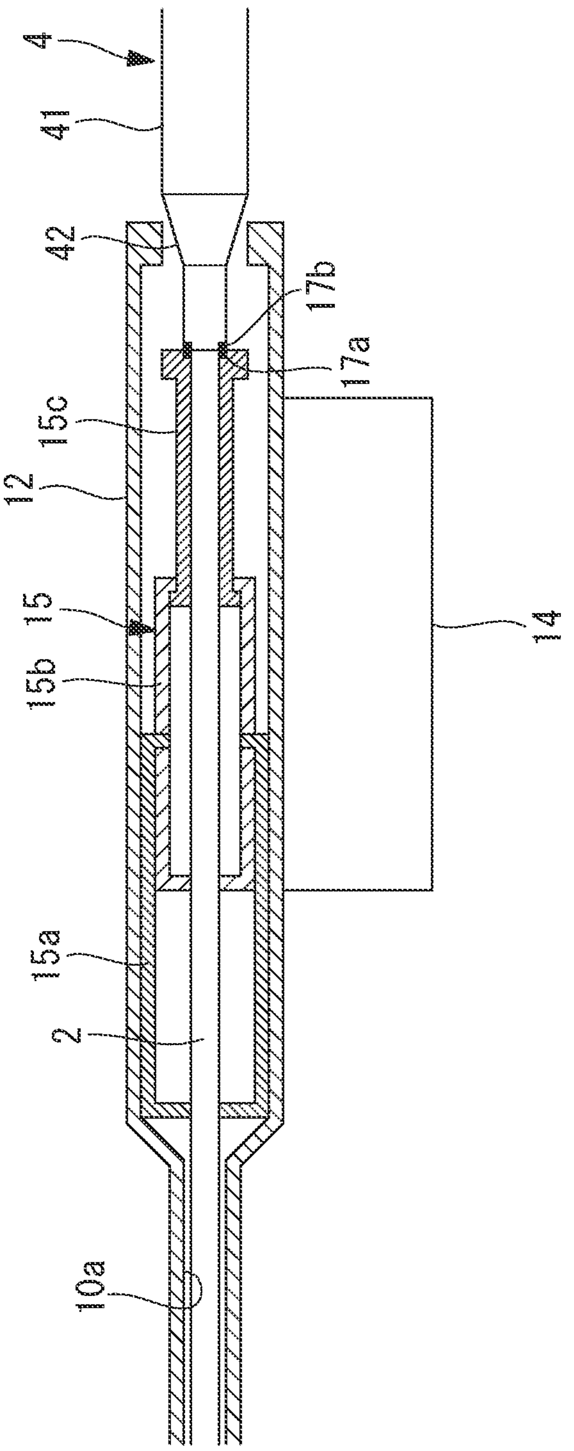
FIG. 9 is a partial longitudinal sectional view of another modification of the access device.

The extension means for extending the telescopic structure 15 may be a mechanism for fixing the inner pipe 15*c* to the treatment tool 1, instead of the springs 16*a* and 16*b*. For example, as shown in FIG. 9, the extension means may include magnets 17*a* and 17*b*, which are provided at the proximal end of the inner pipe 15*c* and the distal end of the rigid shaft 4 and generate a magnetic attractive force therebetween.

Although the resistance generating parts generate resistance by means of an elastic restoring force generated by elastic deformation of at least a portion of the resistance generating parts in this embodiment, instead, resistance may be generated by another method. For example, the resistance generating parts may be provided on at least one of the outer circumferential surface of the rigid shaft 4 and the inner circumferential surface of the holder 12 and may include a high-friction material that generates friction as resistance.

When the telescopic structure 15 is provided in the holder 12, the resistance generating parts 20 may be provided on the telescopic structure 15.

Figure 10:
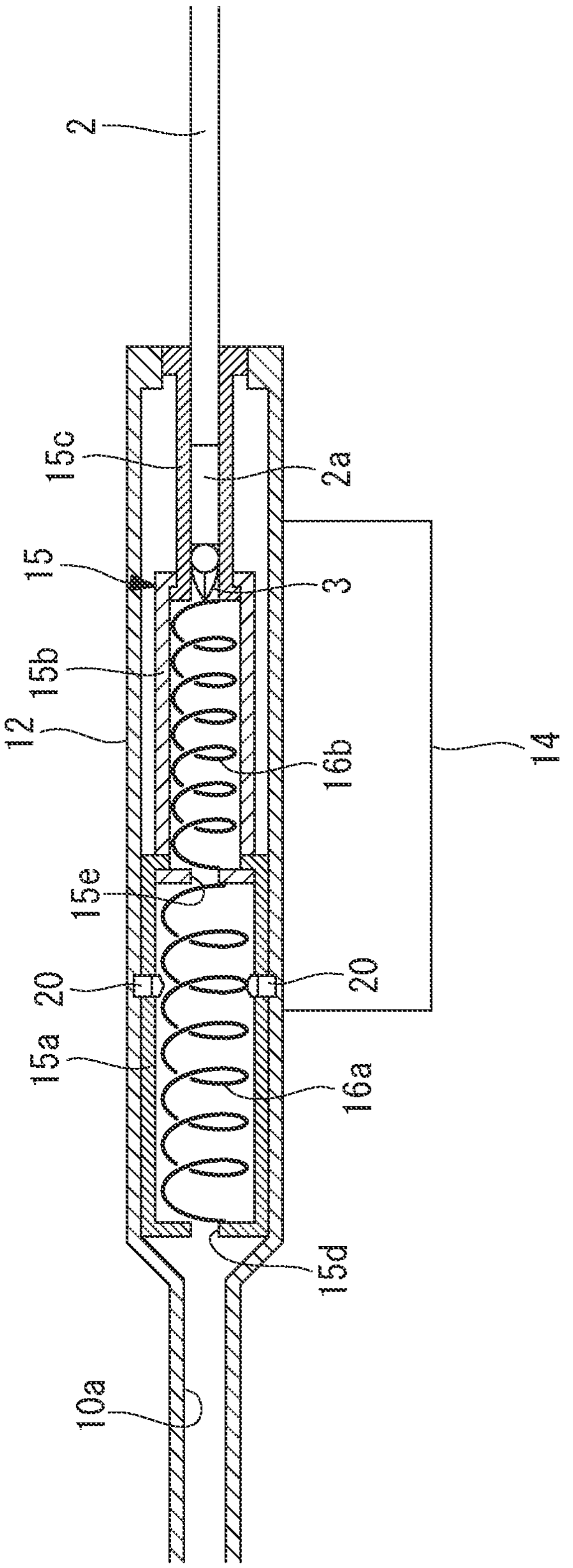
FIG. 10 is a partial longitudinal sectional view of another modification of the access device.

For example, as shown in FIG. 10, the resistance generating parts 20 may be provided on the outer pipe 15*a* and may be configured to elastically contract by contact with the intermediate pipe 15*b*. With this configuration, the doctor B can feel resistance when the advancing intermediate pipe 15*b* goes over the resistance generating parts 20 protruding from the inner surface of the outer pipe 15*a*. Accordingly, the doctor B can intuitively recognize the approach of the distal end of the treatment tool 1 to the vicinity of the distal end of the flexible tube 11.

The springs 16*a* and 16*b* may be made to function as resistance generating parts by differentiating the spring constants of the springs 16*a* and 16*b* from each other.

More specifically, the spring 16*a* in the outer pipe 15*a* has a greater spring constant than the spring 16*b* in the intermediate pipe 15*b*. As the rigid shaft 4 is advanced, the spring 16*b* is preferentially compressed first, and after the spring 16*b* is compressed to some extent, the spring 16*a* is compressed. The compression of the spring 16*a* increases the resistance. By setting the spring constant of the spring 16*a* to such an extent that the doctor B can recognize an increase in the resistance, the doctor B can intuitively recognize the approach of the distal end of the treatment tool 1 to the vicinity of the distal end of the flexible tube 11.

The following aspects can be derived from the embodiments.

According to an aspect of the present invention, there is provided a medical manipulator system including: a treatment tool having a long flexible shaft and a rigid shaft connected to a proximal end of the flexible shaft; an access device that guides the treatment tool and that has a long flexible tube, into which the flexible shaft is inserted, and a rigid sheath, which is connected to a proximal end of the flexible tube and into which the flexible shaft and the rigid shaft are inserted; and a resistance generating part that is provided on at least one of the rigid shaft and the sheath and that generates resistance to advancing of the rigid shaft through the sheath. The resistance generated by the resistance generating part increases when a distal end of the advancing treatment tool passes through a distal end of the flexible tube or a vicinity of the distal end of the flexible tube inside the flexible tube, and the resistance generated by the resistance generating part decreases after the distal end of the advancing treatment tool passes through the distal end of the flexible tube or the vicinity.

The flexible tube of the access device is inserted into the body, and the rigid sheath of the access device is disposed outside the body. Accordingly, a path for the treatment tool from the outside of the body to the target position inside the body is ensured inside the access device. An operator, such as a doctor, inserts the flexible shaft into the flexible tube until the rigid shaft is disposed inside the sheath. In this state, the rigid shaft is stably supported and guided by the rigid sheath of the access device. Hence, the operator can easily perform advancing/retracting operations of the treatment tool.

In this case, when the distal end of the treatment tool advancing through the flexible tube passes through the distal end of the flexible tube or the vicinity thereof, in other words, when or immediately before the distal end of the treatment tool protrudes from the distal end of the access device, the resistance generated by the resistance generating part provided on at least one of the rigid shaft and the sheath increases. The increase in the resistance is efficiently transmitted, via the rigid shaft, to the hand of the operator gripping the treatment tool at or near the rigid shaft. Accordingly, the operator who is operating the treatment tool can reliably recognize the timing when the distal end of the treatment tool protrudes from the distal end of the access device.

Furthermore, because the resistance decreases after the distal end of the treatment tool protrudes from the distal end of the access device, in a state in which the distal end of the treatment tool protrudes from the distal end of the access device, the treatment tool can be smoothly advanced.

In the above aspect, it is preferable that the resistance generated by the resistance generating part gradually increase as the distal end of the advancing treatment tool approaches the distal end of the flexible tube or the vicinity, and become maximum when a distal end of the treatment tool passes through the distal end of the flexible tube or the vicinity.

With this configuration, the operator can more reliably recognize the timing when the treatment tool protrudes from the distal end of the access device on the basis of a change in the magnitude of the resistance.

In the above-described aspect, the rigid shaft may have a parallel surface extending parallel to a longitudinal axis of the sheath, and the resistance generated by the resistance generating part may decrease to a constant magnitude after the distal end of the advancing treatment tool passes through the distal end of the flexible tube or the vicinity.

With this configuration, the resistance decreases after the distal end of the treatment tool protrudes from the distal end of the access device, and the magnitude of the resistance is maintained constant by the interaction between the resistance generating part and the parallel surface. Hence, in a state in which the distal end of the treatment tool protrudes from the distal end of the access device, the treatment tool can be advanced with a constant force.

In the above aspect, the resistance generating part may protrude radially inward from an inner circumferential surface of the sheath, at least a portion of the resistance generating part may be an elastic member that is elastically deformed by contact between the resistance generating part and the rigid shaft, and the resistance generating part may be provided at such a position that a distal end of the rigid shaft passes through the resistance generating part when the distal end of the advancing treatment tool passes through the distal end of the flexible tube or the vicinity.

With this configuration, when the distal end of the advancing treatment tool passes through the distal end of the access device or the vicinity thereof, the resistance generating part comes into contact with the rigid shaft, and the elastic member is elastically deformed, generating an elastic restoring force, serving as resistance. Furthermore, friction, serving as resistance, is generated between the resistance generating part and the rigid shaft. In this way, the resistance can be mechanically generated with a simple structure.

In the above-described aspect, an end face of the resistance generating part may be a spherical surface, and the resistance may be a component force, in a longitudinal direction of the rigid shaft, of an elastic restoring force with which the resistance generating part presses the rigid shaft in a radial direction.

With this configuration, in which the end face of the resistance Generating part comes into point contact with the cuter surface of the rigid shaft after the distal end of the treatment tool protrudes from the distal end of the access device, the friction, serving as resistance, can be reduced to substantially zero.

In the above-described configuration, the rigid shaft may have an inclined surface inclined so as to be gradually displaced radially outward from a side of the distal end toward a side of a proximal end with respect to a longitudinal axis of the rigid shaft, the inclined surface may be connected, on a side of a proximal end of the inclined surface, to a distal end of a parallel surface extending toward the side of the proximal end of the rigid shaft, and the resistance may be a component force, in a longitudinal direction of the rigid shaft, of an elastic restoring force with which the resistance generating part presses the rigid shaft in a radial direction.

With this configuration, the resistance generating part comes into contact with the inclined surface and then comes into contact with the parallel surface. The resistance generating part is elastically deformed by contact with the inclined surface and generates a component force of an elastic restoring force, serving as resistance. Because the inclined surface is gradually displaced radially outward from the distal side toward the proximal side, the amount of elastic deformation and the elastic restoring force of the elastic member increase, and thus the resistance increases, as the rigid shaft advances through the sheath. Thus, the resistance can be gradually increased as the treatment tool is advanced. Furthermore, when the resistance generating part is in contact with the parallel surface, a component force of the elastic restoring force is not generated, and, because the amount of elastic deformation of the resistance generating part is constant, the magnitude of the friction is constant. Hence, after the distal end of the treatment tool passes through the distal end of the access device or the vicinity thereof, the resistance can be decreased, and the magnitude of the resistance can be made constant.

In the above-described configuration, the resistance generating part may be formed of a resin material and may be elastically deformed in at least one of a longitudinal direction and a radial direction of the rigid sheath by contact with the rigid shaft.

With this configuration, when the resistance generating part is elastically deformed in the longitudinal direction of the sheath, an elastic restoring force in the longitudinal direction of the rigid shaft, serving as resistance, can be generated. Furthermore, when the resistance generating part is elastically deformed in the radial direction of the sheath, friction, serving as resistance, can be generated.

REFERENCE SIGNS LIST

1 treatment tool
2 flexible shaft
4 rigid shaft
41*a* outer circumferential surface (parallel surface)
42*a* outer circumferential surface (inclined surface)
10 access device
11 flexible tube
12 holder (sheath)
20 resistance generating part
22 elastic member, spring

The invention claimed is:

1. A medical manipulator system comprising:
a treatment tool having a long flexible shaft and a rigid shaft connected to a proximal end of the flexible shaft;
an access device that guides the treatment tool and that has a long flexible tube, into which the flexible shaft is inserted, and a rigid sheath, which is connected to a proximal end of the flexible tube and into which the flexible shaft and the rigid shaft are inserted; and
a resistance generating part that is provided on at least one of the rigid shaft and the sheath and that generates resistance to advancing of the rigid shaft through the sheath,
wherein the resistance generated by the resistance generating part increases when a distal end of the advancing treatment tool passes through a distal end of the flexible tube or a vicinity of the distal end of the flexible tube inside the flexible tube, and
the resistance generated by the resistance generating part decreases after the distal end of the advancing treatment tool passes through the distal end of the flexible tube or the vicinity.

2. The medical manipulator system according to claim 1, wherein the resistance generated by the resistance generating part gradually increases as the distal end of the advancing treatment tool approaches the distal end of the flexible tube or the vicinity, and becomes maximum when a distal end of the treatment tool passes through the distal end of the flexible tube or the vicinity.

3. The medical manipulator system according to claim 1, wherein the rigid shaft has a parallel surface extending parallel to a longitudinal axis of the sheath, and
the resistance generated by the resistance generating part decreases to a constant magnitude after the distal end of the advancing treatment tool passes through the distal end of the flexible tube or the vicinity.

4. The medical manipulator system according to claim 1, wherein
the resistance generating part protrudes radially inward from an inner circumferential surface of the sheath, at least a portion of the resistance generating part is an elastic member that is elastically deformed by contact between the resistance generating part and the rigid shaft, and
the resistance generating part is provided at such a position that a distal end of the rigid shaft passes through the resistance generating part when the distal end of the advancing treatment tool passes through the distal end of the flexible tube or the vicinity.

5. The medical manipulator system according to claim 4, wherein
an end face of the resistance generating part is a spherical surface, and
the resistance is a component force, in a longitudinal direction of the rigid shaft, of an elastic restoring force with which the resistance generating part presses the rigid shaft in a radial direction.

6. The medical manipulator system according to claim 4, wherein
the rigid shaft has an inclined surface inclined so as to be gradually displaced radially outward from a side of the distal end toward a side of a proximal end with respect to a longitudinal axis of the rigid shaft,
the inclined surface is connected, on a side of a proximal end of the inclined surface, to a distal end of a parallel surface extending toward the side of the proximal end of the rigid shaft, and
the resistance is a component force, in a longitudinal direction of the rigid shaft, of an elastic restoring force with which the resistance generating part presses the rigid shaft in a radial direction.

7. The medical manipulator system according to claim 5, wherein the resistance generating part is formed of a resin material and is elastically deformed in at least one of a longitudinal direction and a radial direction of the rigid sheath by contact with the rigid shaft.

8. The medical manipulator system according to claim 6, wherein a distance from the distal end of the flexible tube to the resistance generating part is equal to or larger than a distance from a distal end of the treatment tool to the proximal end of the inclined surface.

* * * * *